United States Patent
Hawkins et al.

(10) Patent No.: US 9,044,618 B2
(45) Date of Patent: *Jun. 2, 2015

(54) SHOCKWAVE VALVULOPLASTY CATHETER SYSTEM

(75) Inventors: Daniel Hawkins, Fremont, CA (US); John M. Adams, Snohomish, WA (US)

(73) Assignee: SHOCKWAVE MEDICAL, INC., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/611,997

(22) Filed: Nov. 4, 2009

(65) Prior Publication Data

US 2010/0114020 A1 May 6, 2010

Related U.S. Application Data

(60) Provisional application No. 61/111,600, filed on Nov. 5, 2008.

(51) Int. Cl.
| | | |
|---|---|---|
| *A61B 17/22* | (2006.01) | |
| *A61N 1/38* | (2006.01) | |
| *A61M 25/10* | (2013.01) | |
| *A61N 1/05* | (2006.01) | |

(52) U.S. Cl.
CPC .............. *A61N 1/38* (2013.01); *A61M 25/1002* (2013.01); *A61M 2025/1072* (2013.01); *A61N 1/056* (2013.01); *A61B 17/22022* (2013.01); *A61B 2017/22025* (2013.01); *A61B 2017/22098* (2013.01)

(58) Field of Classification Search
CPC .............. A61B 2018/0022; A61B 2018/00214; A61B 2018/00244; A61B 2018/00232; A61B 17/320068; A61B 17/22004; A61B 17/22012; A61B 17/22029; A61B 17/22022
USPC ........... 606/41, 108, 127–129, 170, 191, 194; 604/22, 96.01; 623/1.11; 126/41, 108, 126/127–129, 170, 191, 194

See application file for complete search history.

(56) References Cited

U.S. PATENT DOCUMENTS

| | | | |
|---|---|---|---|
| 3,413,976 A | | 12/1968 | Roze |
| 3,785,382 A | | 1/1974 | Schmidt-Kloiber et al. |
| 3,902,499 A | | 9/1975 | Shene |
| 4,027,674 A | * | 6/1977 | Tessler et al. .............. 606/128 |
| 4,030,505 A | * | 6/1977 | Tessler .................... 606/128 |

(Continued)

FOREIGN PATENT DOCUMENTS

| | | |
|---|---|---|
| CN | 101043914 | 9/2007 |
| DE | 3038445 A1 | 5/1982 |

(Continued)

OTHER PUBLICATIONS

U.S. Appl. No. 61/061,170, filed Jun. 13, 2008 and expired on Jun. 13, 2009.

(Continued)

*Primary Examiner* — Sarah W Aleman
(74) *Attorney, Agent, or Firm* — Morrison & Foerster LLP

(57) ABSTRACT

A valvuloplasty system comprises a balloon adapted to be placed adjacent leaflets of a valve. The balloon is inflatable with a liquid. The system further includes a shock wave generator within the balloon that produces shock waves. The shock waves propagate through the liquid and impinge upon the valve to decalcify and open the valve.

10 Claims, 2 Drawing Sheets

(56) References Cited

U.S. PATENT DOCUMENTS

| | | | |
|---|---|---|---|
| 4,662,126 A | 5/1987 | Malcolm | |
| 4,671,254 A | 6/1987 | Fair | |
| 4,685,458 A | 8/1987 | Leckrone | |
| 4,809,682 A | 3/1989 | Forssmann et al. | |
| 4,878,495 A | 11/1989 | Grayzel et al. | |
| 5,009,232 A | 4/1991 | Hassler et al. | |
| 5,046,503 A | 9/1991 | Schneiderman | |
| 5,057,103 A | 10/1991 | Davis | |
| 5,078,717 A | 1/1992 | Parins et al. | |
| 5,103,804 A | 4/1992 | Abele et al. | |
| 5,152,767 A | 10/1992 | Sypal et al. | |
| 5,152,768 A | 10/1992 | Bhatta | |
| 5,154,722 A * | 10/1992 | Filip et al. | 606/128 |
| 5,176,675 A | 1/1993 | Watson et al. | |
| 5,195,508 A * | 3/1993 | Muller et al. | 606/128 |
| 5,246,447 A | 9/1993 | Rosen et al. | |
| 5,281,231 A | 1/1994 | Rosen et al. | |
| 5,295,958 A * | 3/1994 | Shturman | 606/159 |
| 5,324,255 A | 6/1994 | Passafaro et al. | |
| 5,336,234 A | 8/1994 | Vigil et al. | |
| 5,368,591 A * | 11/1994 | Lennox et al. | 606/27 |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,505,702 A | 4/1996 | Arney | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | de la Torre et al. | |
| 5,846,218 A | 12/1998 | Brisken et al. | |
| 6,007,530 A | 12/1999 | Doernhoefer et al. | |
| 6,033,371 A | 3/2000 | Torre et al. | |
| 6,083,232 A | 7/2000 | Cox | |
| 6,113,560 A * | 9/2000 | Simnacher | 601/4 |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 * | 9/2001 | Brisken et al. | 604/22 |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de La Torre et al. | |
| 6,440,061 B1 | 8/2002 | Wenner et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,689,089 B1 | 2/2004 | Tiedtke et al. | |
| 6,736,784 B1 * | 5/2004 | Menne et al. | 606/128 |
| 6,740,081 B2 | 5/2004 | Hilal | |
| 6,755,821 B1 * | 6/2004 | Fry | 606/15 |
| 6,989,009 B2 | 1/2006 | Lafontaine | |
| 7,241,295 B2 | 7/2007 | Maguire | |
| 7,569,032 B2 | 8/2009 | Naimark et al. | |
| 7,618,432 B2 | 11/2009 | Pedersen et al. | |
| 8,162,859 B2 | 4/2012 | Schultheiss et al. | |
| 8,556,813 B2 | 10/2013 | Cioanta et al. | |
| 8,574,247 B2 | 11/2013 | Adams et al. | |
| 8,728,091 B2 | 5/2014 | Hakala et al. | |
| 8,747,416 B2 | 6/2014 | Hakala et al. | |
| 2001/0044596 A1 | 11/2001 | Jaafar | |
| 2002/0177889 A1 | 11/2002 | Brisken et al. | |
| 2003/0163081 A1 | 8/2003 | Constantz et al. | |
| 2003/0229370 A1 | 12/2003 | Miller | |
| 2004/0044308 A1 | 3/2004 | Naimark et al. | |
| 2004/0082859 A1 | 4/2004 | Schaer | |
| 2004/0097996 A1 | 5/2004 | Rabiner et al. | |
| 2004/0249401 A1 | 12/2004 | Rabiner et al. | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0090846 A1 | 4/2005 | Pedersen et al. | |
| 2005/0171527 A1 * | 8/2005 | Bhola | 606/41 |
| 2005/0245866 A1 | 11/2005 | Azizi | |
| 2005/0251131 A1 | 11/2005 | Lesh | |
| 2006/0004286 A1 | 1/2006 | Chang et al. | |
| 2006/0074484 A1 | 4/2006 | Huber | |
| 2006/0184076 A1 | 8/2006 | Gill et al. | |
| 2006/0190022 A1 * | 8/2006 | Beyar et al. | 606/192 |
| 2007/0088380 A1 | 4/2007 | Hirszowicz et al. | |
| 2007/0129667 A1 | 6/2007 | Tiedtke et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2007/0299481 A1 | 12/2007 | Syed et al. | |
| 2008/0077165 A1 | 3/2008 | Murphy | |
| 2008/0097251 A1 | 4/2008 | Babaev | |
| 2009/0030503 A1 | 1/2009 | Ho | |
| 2009/0247945 A1 | 10/2009 | Levit et al. | |
| 2009/0254114 A1 | 10/2009 | Hirszowics et al. | |
| 2009/0312768 A1 | 12/2009 | Hawkins | |
| 2010/0016862 A1 | 1/2010 | Hawkins et al. | |
| 2010/0036294 A1 | 2/2010 | Mantell et al. | |
| 2010/0094209 A1 | 4/2010 | Drasler et al. | |
| 2010/0114065 A1 | 5/2010 | Hawkins et al. | |
| 2010/0121322 A1 | 5/2010 | Swanson | |
| 2010/0305565 A1 | 12/2010 | Truckai et al. | |
| 2010/0324554 A1 | 12/2010 | Gifford et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0295227 A1 | 12/2011 | Hawkins et al. | |
| 2012/0116289 A1 | 5/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0116714 A1 | 5/2013 | Adams et al. | |
| 2014/0214061 A1 | 7/2014 | Adams et al. | |
| 2014/0243820 A1 | 8/2014 | Adams et al. | |

FOREIGN PATENT DOCUMENTS

| | | |
|---|---|---|
| EP | 0442199 A2 | 8/1991 |
| EP | 0571306 A1 | 11/1993 |
| JP | 62-275446 A | 11/1987 |
| JP | 3-63059 A | 3/1991 |
| JP | 6-125915 A | 5/1994 |
| JP | 7-47135 A | 2/1995 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-81374 A | 3/2004 |
| JP | 2004-357792 A | 12/2004 |
| JP | 2005-95410 A | 4/2005 |
| JP | 2005-515825 A | 6/2005 |
| JP | 2006-516465 A | 7/2006 |
| JP | 2008-506447 A | 3/2008 |
| JP | 2011-528963 A | 12/2011 |
| WO | 96/24297 A1 | 8/1996 |
| WO | 2004/069072 A2 | 8/2004 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A2 | 10/2009 |
| WO | 2009/152352 A2 | 12/2009 |
| WO | 2010/014515 A2 | 2/2010 |
| WO | 2010/014515 A3 | 8/2010 |
| WO | 2011/069025 A1 | 6/2011 |
| WO | 2011/143468 A2 | 11/2011 |
| WO | 2013/070750 A1 | 5/2013 |

OTHER PUBLICATIONS

International Search Report Dated Jun. 11, 2010, for International Patent Application No. PCT/US2009/063354.

Supplementary European Search Report for European Application No. EP09825393, European Patent Office, Munich, Feb. 20, 2013, pp. 2.

(56) References Cited

OTHER PUBLICATIONS

International Search Report received for PCT Patent Application No. PCT/US2009/047070, mailed on Jan. 19, 2010, 4 pages.
International Written Opinion received for PCT Patent Application No. PCT/US2011/047070, mailed on May 1, 2012, 5 pages.
International Preliminary Report on Patentability received for PCT Patent Application No. PCT/US2011/047070, mailed on Feb. 21, 2013, 7 pages.
International Written Opinion received for PCT Patent Application No. PCT/US2009/063354, mailed on Jun. 11, 2010, 4 pages.
International Preliminary Report on Patentability received for PCT Patent Application No. PCT/US2009/063354, mailed on May 19, 2011, 6 pages.
International Search Report and Written Opinion received for PCT Patent Application No. PCT/US2011/051606, mailed on Apr. 24, 2012, 9 pages.
International Preliminary Report on Patentability received for PCT Patent Application No. PCT/US2011/051606, issued on May 14, 2013, 6 pages.
International Search Report received for PCT Patent Application No. PCT/US2012/023172, mailed on Sep. 28, 2012, 3 pages.
International Search Report received for PCT Patent Application No. PCT/US2012/063925, mailed on Mar. 25, 2013, 3 pages.
International Search Report and Written Opinion received for PCT Patent Application No. PCT/US2013/031805 mailed on May 20, 2013, 13 pages.
Adams et al., U.S. Appl. No. 13/534,658, filed Jun. 27, 2012, titled "Shock Wave Balloon Catheter with Multiple Shock Wave Sources".
Hakala et al., U.S. Appl. No. 13/831,543, filed Mar. 14, 2013, titled "Low Profile Electrodes for an Angioplasty Shock Wave Catheter", 52 pages.
Non Final Office Action received for U.S. Appl. No. 12/482,995, mailed on Jul. 12, 2013, 11 pages.
Office Action received for Australian Patent Application No. 2009257368, issued on Jul. 31, 2013, 4 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages of Official copy only.
Office Action received for Japanese Patent Application No. 2011-513694, mailed on Aug. 27, 2013, 6 pages (3 pages of English Translation and 3 pages of Official copy).
Office Action received for Japanese Patent Application No. 2011-534914, mailed on Oct. 1, 2013, 5 pages (2 pages of English Translation and 3 pages of Official copy).
Notice of Allowance received for U.S. Appl. No. 13/291,875, mailed on Sep. 17, 2013, 11 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Extended European Search Report (includes Supplementary European Search Report and Search Opinion) received for European Patent Application No. 09763640.1, mailed on Oct. 10, 2013, 5 pages.
Final Office Action received for U.S. Appl. No. 13/207,381, mailed on Nov. 7, 2013, 7 pages.
Notice of Allowance received for U.S. Appl. No. 14/046,635, mailed on Dec. 17, 2013, 7 pages.
Office Action received for Australian Patent Application No. 2009313507, issued on Nov. 13, 2013, 3 pages.
Adams et al., U.S. Appl. No. 14/046,635, filed Oct. 4, 2013, titled "Shock Wave Valvuloplasty Device with Moveable Shock Wave Generator".
Adams, John M., U.S. Appl. No. 13/962,315, filed Aug. 8, 2013, titled "Shockwave Valvuloplasty with Multiple Balloons".
Hakala et al., U.S. Appl. No. 14/061,554, filed Oct. 23, 2013, titled "Low Profile Electrodes for an Angioplasty Shock Wave Catheter".
Hawkins et al., U.S. Appl. No. 13/957,276, filed Aug. 1, 2013, titled "Shockwave Catheter".
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/053292, mailed on Nov. 4, 2013, 14 pages.
International Search Report and Written Opinion received for PCT Patent Application No. PCT/US2013/054104, mailed on Oct. 22, 2013, 12 pages.
Non Final Office Action received for U.S. Appl. No. 12/482,995, mailed on Aug. 13, 2014, 10 pages.
Final Office Action received for U.S. Appl. No. 13/049,199 mailed on Aug. 11, 2014, 8 pages.
Notice of Allowance received for U.S. Appl. No. 13/831,543, mailed on Oct. 8, 2014, 14 pages.
Non-Final Office Action received for U.S. Appl. No. 14/271,342, mailed on Sep. 2, 2014, 6 pages.
Notice of Acceptance Received for Australian Patent Application No. 2009257368, mailed on Aug. 28, 2014, 2 pages.
Office Action Received for Japanese Patent Application No. 2011-513694, mailed on Jun. 10, 2014, 2 pages of Official copy only (See Communication under 37 CFR § 1.98(a) (3)).
Office Action Received for Japanese Patent Application No. 2011-534914, mailed on Jul. 15, 2014, 3 pages (1 page of English Translation and 2 pages of Official copy).
Doug Hakala, "Unpublished U.S. Appl. No. 14/515,130, filed Oct. 15, 2014, titled "Low Profile Electrodes for an Angioplasty Shock Wave Catheter"".
International Preliminary Report on Patentability received for PCT Patent Application No. PCT/US2012/063925, mailed on May 22, 2014, 12 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Written Opinon received for PCT Patent Application No. PCT/US2009/047070, mailed on Jan. 19, 2010, 5 pages.
International Preliminary Report on Patentability received for PCT Patent Application No. PCT/US2009/047070, mailed on Dec. 23, 2010, 7 pages.
Office Action received for Australian Patent Application No. 2009257368, issued on Apr. 28, 2014, 4 pages.
Final Office Action received for U.S. Appl. No. 12/482,995, mailed on Feb. 20, 2014, 11 pages.
Non-Final Office Action received for U.S. Appl. No. 12/501,619, mailed on Jan. 28, 2014, 10 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Adams et al., U.S. Appl. No. 14/229,735, filed Mar. 28, 2014, titled "Shock Wave Valvuloplasty Device with Moveable Shock Wave Generator".
Adams et al., Unpublished U.S. Appl. No. 14/271,342, filed May 6, 2014, titled "Shock Wave Balloon Catheter with Multiple Shock Wave Sources", 21 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.

(56) References Cited

OTHER PUBLICATIONS

Notice of Allowance received for U.S. Appl. No. 12/482,995, mailed on Dec. 24, 2014, 6 pages.
Advisory Action Received for U.S. Appl. No. 13/049,199, mailed on Jun. 7, 2012, 3 pages.
Notice of Allowance received for U.S. Appl. No. 13/049,199, mailed on Dec. 15, 2014, 7 pages.
Non Final Office Action received for U.S. Appl. No. 13/207,381, mailed on Nov. 25, 2014, 5 pages.
Non-Final Office Action received for U.S. Appl. No. 13/465,264, mailed on Dec. 23, 2014, 13 pages.
Final Office Action received for U.S. Appl. No. 13/646,570, mailed on Dec. 23, 2014, 10 pages.
Final Office Action received for U.S. Appl. No. 14/271,342 mailed on Feb. 27, 2015, 7 pages.
Notice of Acceptance Received for Australian Patent Application No. 2009313507, mailed on Nov. 17, 2014, 2 pages.
Decision to Grant received for Japanese Patent Application No. 2011-513694, mailed on Oct. 7, 2014, 3 pages of Official copy only (See Communication under 37 CFR § 1.98(a) (3)).
Office Action Received for Japanese Patent Application No. 2011-534914, mailed on Jan. 13, 2015, 9 pages (7 pages of English Translation and 2 pages of Official copy only).
International Written Opinion received for PCT Patent Application No. PCT/US2012/063925, mailed on Mar. 25, 2013, 9 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/053292, mailed on Feb. 19, 2015, 9 pages.

\* cited by examiner

SHOCKWAVE VALVULOPLASTY CATHETER SYSTEM

CLAIM OF PRIORITY

The present application claims the benefit of U.S. Provisional Patent Application Ser. No. 61/111,600, filed Nov. 5, 2008, which application is incorporated herein by reference in its entirety.

BACKGROUND OF THE INVENTION

Aortic calcification, also called aortic sclerosis, is a buildup of calcium deposits on the aortic valve in the heart. This often results in a heart murmur, which can easily be heard with a stethoscope over the heart. However, aortic calcification usually doesn't significantly affect the function of the aortic valve.

In some cases, though, the calcium deposits thicken and cause narrowing at the opening of the aortic valve. This impairs blood flow through the valve, causing chest pain or a heart attack. Doctors refer to such narrowing as aortic stenosis.

Aortic calcification typically affects older adults. But when it occurs in younger adults, it's often associated with an aortic valve defect that is present at birth (congenital) or with other illnesses such as kidney failure. An ultrasound of the heart (echocardiogram) can determine the severity of aortic calcification and also check for other possible causes of a heart murmur.

At present there is no specific treatment for aortic calcification. General treatment includes the monitoring for further developments of heart disease. Cholesterol levels are also checked to determine the need for medications to lower cholesterol in the hope to prevent progression of aortic calcification. If the valve becomes severely narrowed, aortic valve replacement surgery may be necessary.

The aortic valve area can be opened or enlarged with a balloon catheter (balloon valvuloplasty) which is introduced in much the same way as in cardiac catheterization. With balloon valvuloplasty, the aortic valve area typically increases slightly. Patients with critical aortic stenosis can therefore experience temporary improvement with this procedure. Unfortunately, most of these valves narrow over a six to 18 month period. Therefore, balloon valvuloplasty is useful as a short-term measure to temporarily relieve symptoms in patients who are not candidates for aortic valve replacement. Patients who require urgent noncardiac surgery, such as a hip replacement, may benefit from aortic valvuloplasty prior to surgery. Valvuloplasty improves heart function and the chances of surviving non-cardiac surgery. Aortic valvuloplasty can also be useful as a bridge to aortic valve replacement in the elderly patient with poorly functioning ventricular muscle. Balloon valvuloplasty may temporarily improve ventricular muscle function, and thus improve surgical survival. Those who respond to valvuloplasty with improvement in ventricular function can be expected to benefit even more from aortic valve replacement. Aortic valvuloplasty in these high risk elderly patients has a similar mortality (5%) and serious complication rate (5%) as aortic valve replacement in surgical candidates.

The present invention provides an alternative treatment system for stenotic or calcified aortic valves. As will be seen subsequently, the embodiments described herein provide a more tolerable treatment for aortic stenosis and calcified aortic valves than the currently performed aortic valve replacement. The invention also provides a more effective treatment than current valvuloplasty therapy.

SUMMARY OF THE INVENTION

In one embodiment, a valvuloplasty system comprises a balloon adapted to be placed adjacent leaflets of a valve, the balloon being inflatable with a liquid, and a shock wave generator within the balloon that produces shock waves that propagate through the liquid for impinging upon the valve. The balloon may be adapted to be placed on opposite sides of the valve leaflets or within the valve annulus.

The system may further comprise an elongated tube. The balloon may be at the distal end of the elongated tube.

The balloon may include a first balloon chamber and a second balloon chamber. The first and second balloon chambers may be longitudinally spaced from each other.

The elongated tube may include a lumen. The first and second balloon chambers are in fluid communication with the elongated tube lumen.

The shock wave generator may comprise a first shock wave source within the first balloon chamber and a second shock wave source within the second balloon chamber. The first and second shock wave sources may comprise a first electrical arc generator and a second electrical arc generator. The electrical arc generators may comprise at least one electrode adapted for connection to a voltage pulse generator. Each of the electrical arc generators may comprise an electrode pair adapted for connection to a voltage pulse generator. Each of the electrode pairs may comprise a pair of coaxially arranged electrodes.

They may further comprise a high voltage catheter including the first and second electrical arc generators. The first and second electrical arc generators may be longitudinally spaced from each other for being received within the first and second balloon chambers, respectively.

As mentioned above, the balloon may be adapted to be placed within the valve annulus. To that end, the balloon may have a reduced diameter portion adapted to be received within the valve annulus.

The balloon may be formed of a compliant material. Alternatively, the balloon may be formed of a non-compliant material.

According to another embodiment, a catheter system comprises an elongated carrier and a balloon carried by the elongated carrier. The balloon is arranged to receive a fluid therein that inflates the balloon. The system further includes at least one arc generator including at least one pair of coaxially arranged electrodes within the balloon that forms a mechanical shock wave within the balloon.

The system may further include a cable comprising a center conductor and an outer conductive shield insulated from the inner conductor. A first one of the coaxially arranged electrodes may be at least in part formed by the center conductor of the cable, and a second one of the coaxially arranged electrodes may be at least in part formed by the outer conductive shield of the cable.

According to a further embodiment, a valvuloplasty method for treating a valve having leaflets and an annulus comprises placing a balloon adjacent to the leaflets of the valve, inflating the balloon with a liquid, and producing shock waves within the balloon that propagate through the liquid for impinging upon the valve leaflets and the valve annulus.

The placing steps may be performed by placing the balloon on opposite sides of the valve leaflets. Alternatively the placing step may be performed by placing the balloon within the valve annulus.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
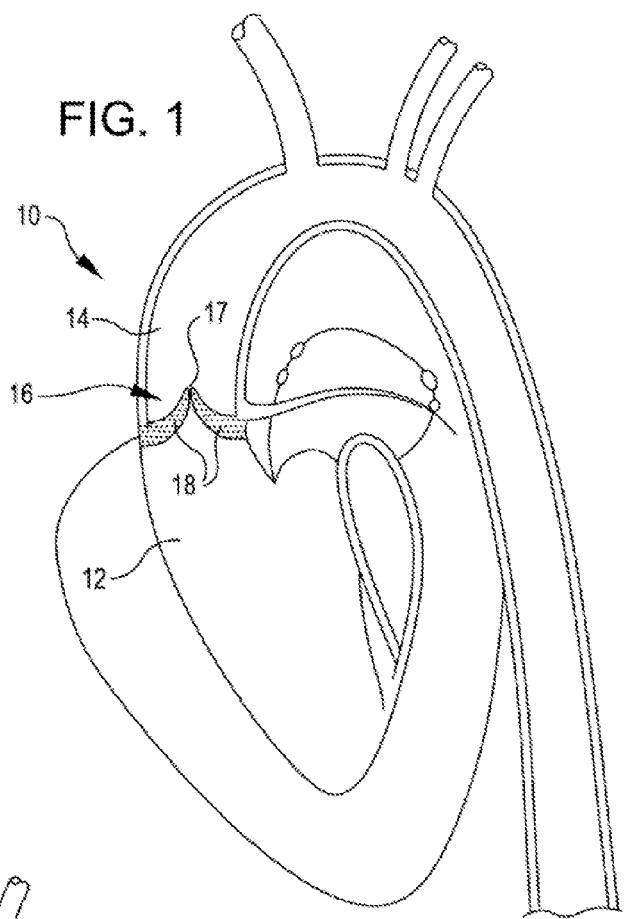
FIG. 1 is a cut away view of the left ventricle, the aorta, and the aortic valve of a heart showing a reduced aortic valve open area and thickened valve leaflets due to calcium and fibrotic tissue.

Referring now to FIG. 1, it is a cut away view of the left ventricle 12, the aorta 14, and the aortic valve 16 of a heart 10 with a stenotic and calcified aortic valve 16. Here more particularly, it may be seen that the opening 17 of the stenotic and calcified aortic valve 16 is restricted in size and that the valve leaflets 18 are thickened with calcium deposits and fibrotic tissue. The thickened leaflets 18 and smaller valve opening 17 restrict blood flow from the heart creating excess work for the heart 10 and poor cardiac output. As previously mentioned, current treatment includes replacement of the valve or attempts too stretch the valve annulus with a balloon.

Figure 2:
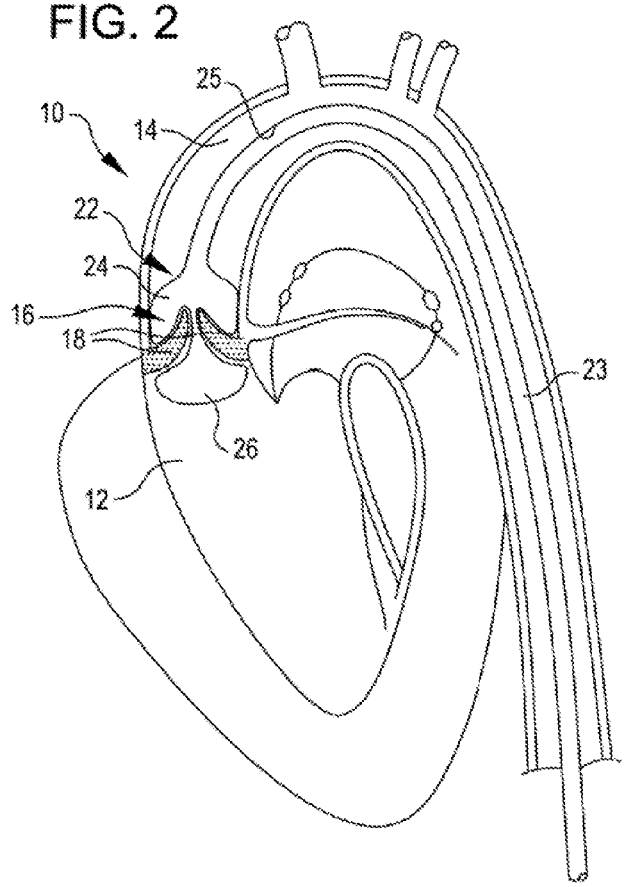
FIG. 2 is a cut away view of the aortic valve of a heart with a treatment balloon placed on both sides of the aortic valve leaflets, according to an embodiment of the present invention.

FIG. 2 is a cut away view of the aortic valve 16 with a treatment balloon 22 placed on both sides of the aortic valve leaflets 18. The balloon 22 may be formed from a compliant or a non-compliant material. The balloon, as seen in FIG. 2, is at the distal end of an elongated tube 23. The treatment balloon 22 has two longitudinally spaced chambers 24 and 26 that share a common inflation lumen 25 of the tube 23. Alternatively the balloon chambers 24 and 26 may not share the same inflation fluid path. The chambers 24 and 26 are longitudinally spaced such that chamber 24 is positioned on one side of the aortic valve leaflets 18 and chamber 26 is positioned on the other side of the aortic valve leaflets 18. The chambers 24 and 26 are inflated with saline/contrast mixture, for example. Each chamber 24 and 26 may contain an electrode (as shall be seen subsequently) that can produce electrical arcs to deliver timed shock waves. The shock waves can be synchronized to concurrently impinge upon both sides of the leaflets 18 to maximize the effectiveness of breaking calcium deposits. Such shock waves may be generated and also synchronized to the R wave of the heart 10 in a manner as described for example in copending application No. 61/061,170 filed on Jun. 13, 2008, which application is incorporated herein in its entirety.

Figure 3:
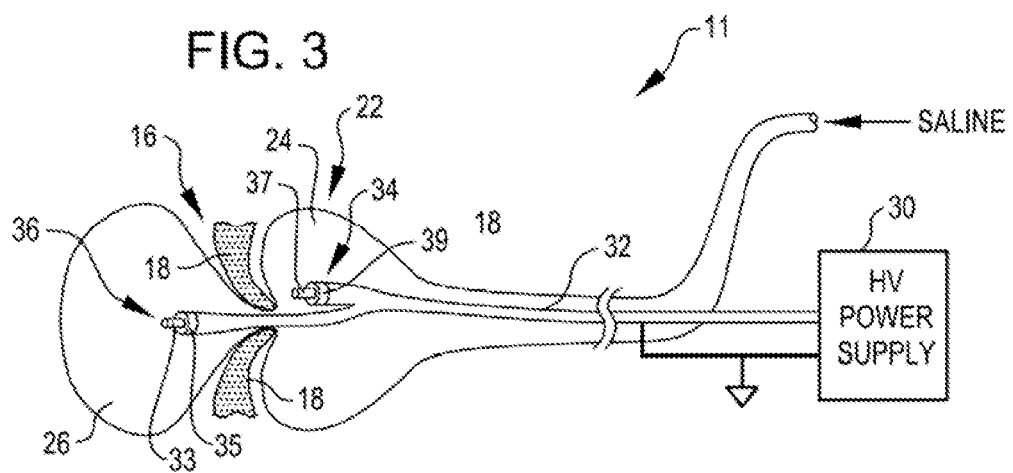
FIG. 3 is a schematic view of a dual shockwave balloon embodying the invention attached to a high voltage power supply.

FIG. 3 is a schematic view of a valvuloplasty system 11 embodying the present invention. The system 11 includes the dual shockwave balloon 22. The balloon 22 has received a high voltage catheter 32 that is connected to a high voltage power supply 30. The schematic representation shows the positioning of the balloon chambers 24 and 26 above and below the leaflets 18 of the aortic valve 16. As previously described, shock waves will impinge upon opposite sides of the leaflets 18 to more effectively break calcium deposits in the valve leaflets 18. The annulus will also be treated in this arrangement. To that end, the high voltage catheter 32 includes electrode pairs 34 and 36 that are coaxially arranged electrodes placed in chambers 24 and 26 respectively of the balloon 22. More specifically, electrode pair 34 is at the distal end of a first cable and comprises a center conductor 33 and an outer conductive shield 35. Similarly, electrode pair 34 is at the distal end of a second cable and comprises a center conductor 37 and an outer conductive shield 39. High voltage pulses from power supply 30 are applied to the electrode pairs 34 and 36 in a manner as described in the aforementioned application Ser. No. 61/061,170 to create shockwaves within the fluid within the chambers 24 and 26 of the balloon 22. The shock waves impinge upon the valve leaflets 18 and the valve annulus to cause the break up of calcium deposits and fibrotic tissue on the valve leaflets 18 and annulus to open the aortic valve 16.

Figure 4:
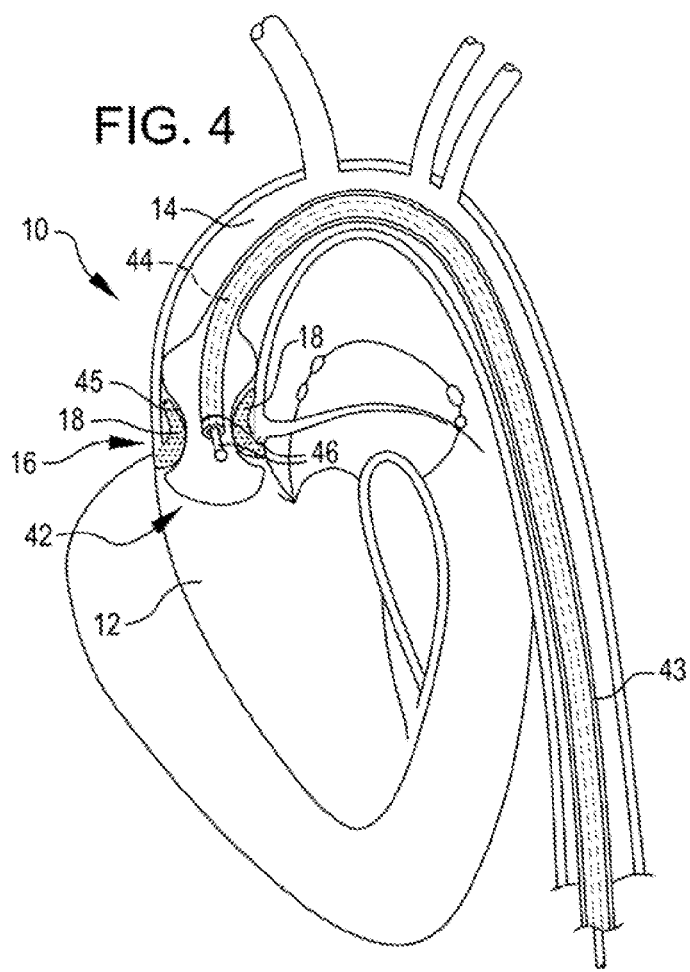
FIG. 4 is a cut away view of a heart showing an alternate valvuloplasty shock wave balloon according to a further embodiment and aspects of the present invention.

FIG. 4 shows an alternate valvuloplasty shock wave balloon 42 at the distal end of an elongated tube 43. The balloon 42 is placed in the annulus of the aortic valve 16. To that end, the balloon 42 has a reduced diameter portion 45 for being received within the valve annulus. The balloon 42 has a high voltage catheter 44 therein that terminates in an electrode pair 46. As in the previous embodiment, the electrode pair 46 may comprise a pair of coaxially arranged electrodes where a center conductor may form at least a part of one electrode and at an outer conductive shield may form at least a part of the other electrode. The catheter 44 and its electrode pair 46 provide shock waves as previously described. Such an arrangement will decalcify the leaflets 18. This not only will decalcify the leaflets 18, but will also soften the aortic valve annulus and expand its diameter. Hence, the balloon 42 provides the added advantage of exerting expansion pressure directly to the annulus of the valve to remodel the annulus diameter.

While particular embodiments of the present invention have been shown and described, modifications may be made, and it is therefore intended to cover all such changes and modifications which fall within the true spirit and scope of the invention.

What is claimed is:

1. An intravascular valvuloplasty system for treating a valve having leaflets and an annulus by breaking calcium deposits on the leaflets and annulus of the valve, each leaflet connected to a wall and having a concave region, comprising:
    an elongate body;
    a balloon being inflatable with a liquid via an inflation lumen of the elongate body, wherein the inflated balloon has a portion shaped to fit within the concave region of a leaflet and between the leaflet and the wall; and
    a shock wave generator having a pair of electrodes located within the balloon that produces a plurality of high voltage pulses across the electrodes to generate electric arcs that create shock waves that propagate through the liquid for impinging upon the valve,
    the balloon being configured to remain intact as the shock waves are produced by the shock wave generator.

2. The system of claim 1, wherein the balloon is at the distal end of the elongate body.

3. The system of claim 1, wherein the shock wave generator has a voltage pulse generator and said pair of electrodes are adapted for connection to the voltage pulse generator.

4. The system of claim 1, wherein the balloon is formed of a compliant material.

5. The system of claim 1, wherein the balloon is formed of a non-compliant material.

6. The system of claim 1, wherein the pair of electrodes include one pair of coaxially arranged electrodes within the balloon.

7. The system of claim 6, further including a cable comprising a center conductor and an outer conductive shield insulated from the inner conductor, wherein a first one of the coaxially arranged electrodes is at least in part formed by the center conductor of the cable, and wherein a second one of the coaxially arranged electrodes is at least in part formed by the outer conductive shield of the cable.

8. The system of claim 1, wherein the shock wave generator within the balloon produces rapidly expanding and collapsing bubbles in the liquid within the balloon that form a plurality of shock waves that propagate through the liquid for impinging upon the valve.

9. The system of claim 1, wherein the balloon is a single layer balloon.

10. The system of claim 1, wherein the pair of electrodes comprises an inner electrode and an outer electrode shield that surrounds the inner electrode.

\* \* \* \* \*